United States Patent [19]

Magherini

[11] 3,966,184

[45] June 29, 1976

[54] DIE-TESTING PRESS

[76] Inventor: Dino Magherini, Via Osservatorio 36, Florence, Italy

[22] Filed: June 3, 1974

[21] Appl. No.: 475,997

[52] U.S. Cl. ............................................ 269/37; 73/103
[51] Int. Cl.² ..................................................... G01N 3/04
[58] Field of Search ................. 73/94, 432 R, 103, 93; 226; 269/43, 86, 87, 87.1, 37, 60; 249/DIG. 4

[56] References Cited
UNITED STATES PATENTS

| | | | |
|---|---|---|---|
| 2,291,106 | 7/1942 | Ruch | 73/93 |
| 3,160,919 | 12/1964 | Carter | 100/214 X |
| 3,535,921 | 10/1970 | Smiley | 73/91 |

*Primary Examiner*—Jerry W. Myracle
*Attorney, Agent, or Firm*—McGlew and Tuttle

[57] ABSTRACT

The press is used for adjusting and testing mating die halves for use in die casting, injection molding and the like, of metals, metal alloys, and synthetic resin materials. The press includes a base formed by a pair of elongated, parallel and facing channels. Each channel has mounted therein, adjacent its lower flange, a respective elongated rigid horizontal guide, and adjustable wedges are provided for horizontally aligning each guide. One guide has a substantially rectangular cross-section and the other guide has a V-shape groove in its upper surface. A pair of fixed substantially planar vertical supports are fixedly mounted on the two channels at opposite ends thereof, and a third substantially planar vertical support is mounted on the two guides for movement toward and away from one of the fixed supports. The movable support and the one fixed support are formed for anchoring thereto of respective die halves of a mating pair. Three elongated axially fixed and non-rotatable screws extend between the two fixed vertical supports and through the movable support. The movable support has three rotatable nuts each threadedly engaged with a respective screw, and a chain drive or the like is provided for rotating the three nuts synchronously. One screw is located at one side of the movable support intermediate the height of the two fixed supports, and the other two screws extend through the movable support at the opposite side thereof, one substantially within the adjacent channel of the base and the other at the extreme upper end of the movable support. Thereby, an adequate space is provided for an operator to enter between the one fixed support and the movable support to mount and dismount the die halves and to adjust the latter.

3 Claims, 7 Drawing Figures

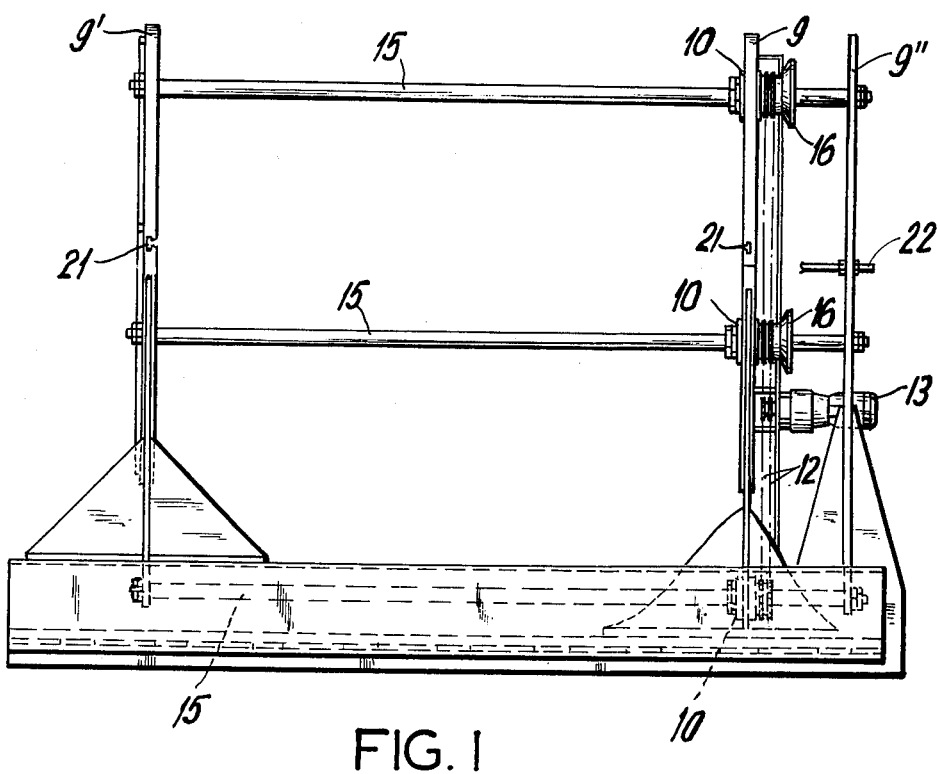
FIG. 1
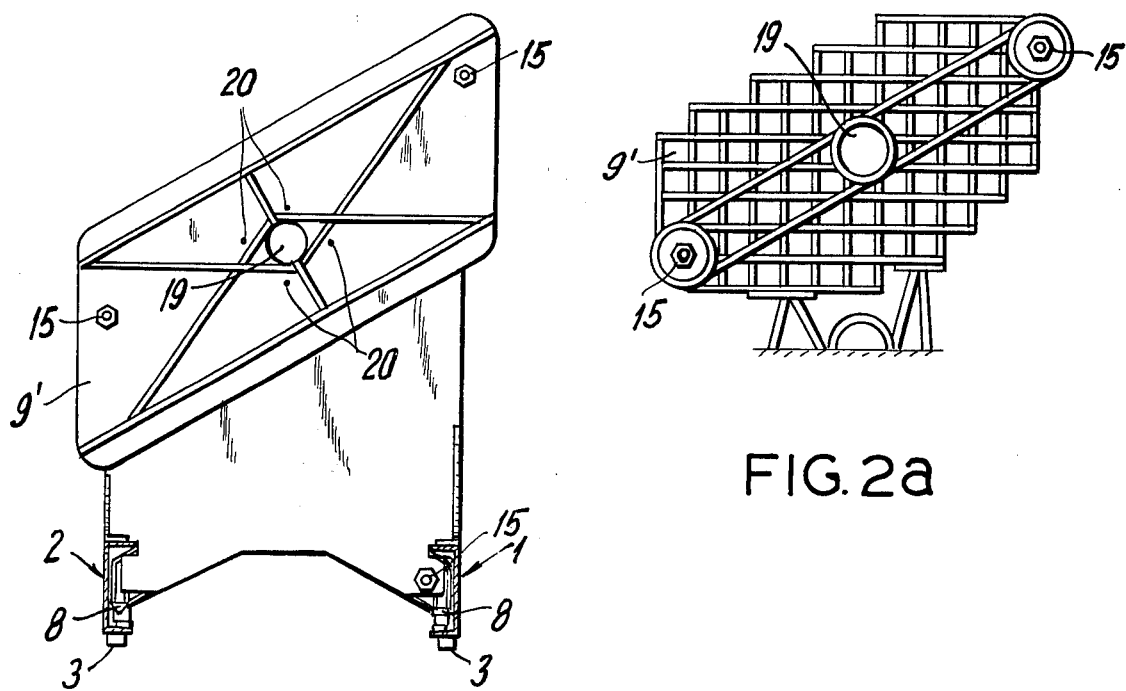
FIG. 2
FIG. 2a

DIE-TESTING PRESS

FIELD AND BACKGROUND OF THE INVENTION

This invention relates to presses and, more particularly, to a novel and improved horizontal type press particularly suited for the adjustment and testing of mating die halves.

It is known that, during the production of dies for stamping, die casting, injection molding and other treatments of metals, metal alloys and synthetic resin materials, it becomes necessary to make a careful adjustment of the two mating die halves in order to ensure a perfect line-up, and to test and inspect the two die halves that form the complete die.

SUMMARY OF THE INVENTION

In accordance with the invention, the press comprises supports for maintaining the two half-dies or die halves, forming the complete die, oriented with their mating plane vertical, one of the die halves being maintained fixed and the other die half being movable in a horizontal direction only. Means are provided to move a movable die half support to a fixed die half support, and this means comprises three screw and nut combinations, the three screws having horizontal and parallel axes and being fixed both axially and against rotation. Thus, the movable support carrying a die half is always perfectly opposed and parallel to the fixed support carrying the other die half. The three nuts are rotatably mounted in the movable support and interconnected by a chain drive for operation by a motor, or by hand, in synchronism with each other.

The three screws are so located, relative to the fixed and movable supports, that it is easy for an operator to enter between the supports, to mount or dismount the die halves into or out of the press, either from above or from the side, and to anchor the die halves to the fixed and movable supports by nesting, strapping, or other anchoring operation. Furthermore, the operator can also enter into the space between the two die halves, when they are properly spaced apart horizontally, for the purpose of performing manual work and using either manual or electric tools directly at any point of the two die halves.

As a further feature of the invention, the press comprises two substantially plane and vertical opposed supports, one of which is fixed and the other of which is movable in a straight horizontal motion, being guided by horizontal skids situated inside two channels which form the base of the machine, the two channels extending longitudinally in spaced parallel and facing relation. The movable support is moved in opposite horizontal directions by the three rotating nuts each engageable with a respective one of the three screws, and the three screws, which extend horizontally and are parallel to each other, are placed at three different positions, that is, at three different levels. The screws are secured at their respective opposite ends to the fixed support and to a vertical frame which is also fixed to the base.

For this construction, the two halves of the die being tested therefore will come together or move apart, and can also be closed more or less and more or less quickly at the will of the operator. The operator, by means of a push button, can control the movements of the press. In practical use, after having brought the two die-carrying supports as close together as possible, so as to close the die, the operator has the possibility to verify the more or less correct operation of the die. Then, having moved the two supports apart, he can enter between the two die halves to undertake the necessary operations of adjustment and lining up, until a correct mechanical functioning, but especially inspection of the die, is obtained.

An object of the invention is to provide an improved horizontal die-testing press for adjusting and testing mating die halves.

Another object of the invention is to provide such a die-testing press including a fixed die half support and a movable die half support, the movable die half support being movable toward and away from the fixed die half support in strict parallelism therewith and strictly horizontal.

A further object of the invention is to provide such a die-testing press which is so designed that an operator can readily enter into the press between the two die halves mounted therein for mounting, dismounting, testing and adjusting the die halves.

For an understanding of the principles of the invention, reference is made to the following description of a typical embodiment thereof as illustrated in the accompanying drawings.

BRIEF DESCRIPTION OF THE DRAWINGS

In the drawings:

FIG. 1 is a somewhat schematic side elevation view of a horizontal die-testing press embodying the invention;

FIG. 2 is a lefthand elevation view of the press shown in FIG. 1 and illustrating one form of vertical support;

FIG. 2a is a view similar to FIG. 2 illustrating a modified form of vertical support;

DESCRIPTION OF THE PREFERRED EMBODIMENT

Figure 6:
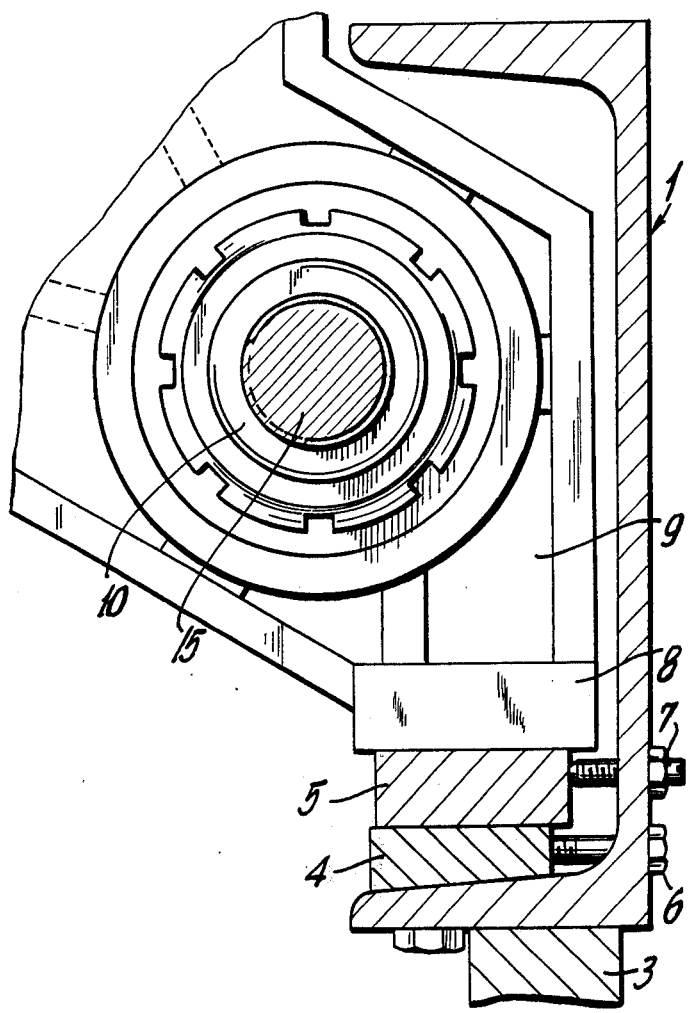
FIG. 6 is a view, similar to FIG. 5, illustrating the other channel forming the base of the press.

Referring more particularly to FIGS. 1 and 2, the horizontal die-testing press embodying the invention rests on the ground, or on a floor, on two elongated facing and parallel channels 1 and 2, on the lower flanges of which there are secured feet or plugs 3 engageable with the ground or the floor. The two channels 1 and 2 form the horizontal rigid base of the die-testing press. As best seen in FIG. 6, wedges 4 are mounted along the inner surface of the lower flange of channel 1 and serve for horizontal alignment and adjustment of a substantially rectangular cross-section longitudinal guide 5 extending through the complete length of beam 1. Guide 5 is adjustable in height by means of the wedges 4 operated by screws or bolts 6, and is fixed in position by means of screws or bolts 7. Guide 5 slidably supports a skid 8 secured to or forming part of a transversely extending movable support 9 which is movable along channels 1 and 2 and is constructed and arranged to support a die half.

The interior of channel 2 is completely symmetrical to the interior of channel 1, except that, in the case of channel 2, guide 5' has an inverted triangular groove in its upper surface and skid 8', secured to or forming part of support 9, has the cross-sectional shape of an inverted triangle. The purpose of this arrangement is to form, in addition to a horizontal guide, a longitudinal guide, thus excluding the danger of jamming of the support planes of the two die halves when the dies are mounted thereon with eccentric friction relative to the centers of the planes or supports.

The planar vertical support 9, whose lower end is constituted by the skids 8 and 8' sliding on the respective guides 5 and 5' has rotatably mounted therein three nuts or female threaded screws 10 to each of which there is secured a double sprocket 11. Sprockets 11 are engaged by endless chains 12 which, when driven by an electric motor 13 fixedly mounted on support 9, transmit the motion to the sprockets 11 so that the nuts 10 are rotated in synchronism with each other. Each nut 10 is mounted loosely in support 9 with the interposition of anti-friction bearings 14, and is in threaded engagement with a respective elongated screw 15 fixed to the supports 9' and 9'' fixedly mounted on the base 1-2 of the die-testing press at opposite ends thereof. Consequently, motor 13 driving chains 12 rotates nuts 10 and nuts 10, turning relative to the respective screws 15, shift support 9 along the guides 5 and 5'. The two upper nuts 10 are also provided with hand wheels 16 which may be used for any small or indexing displacements of support 9, and intended to be effected by hand.

Figure 3:
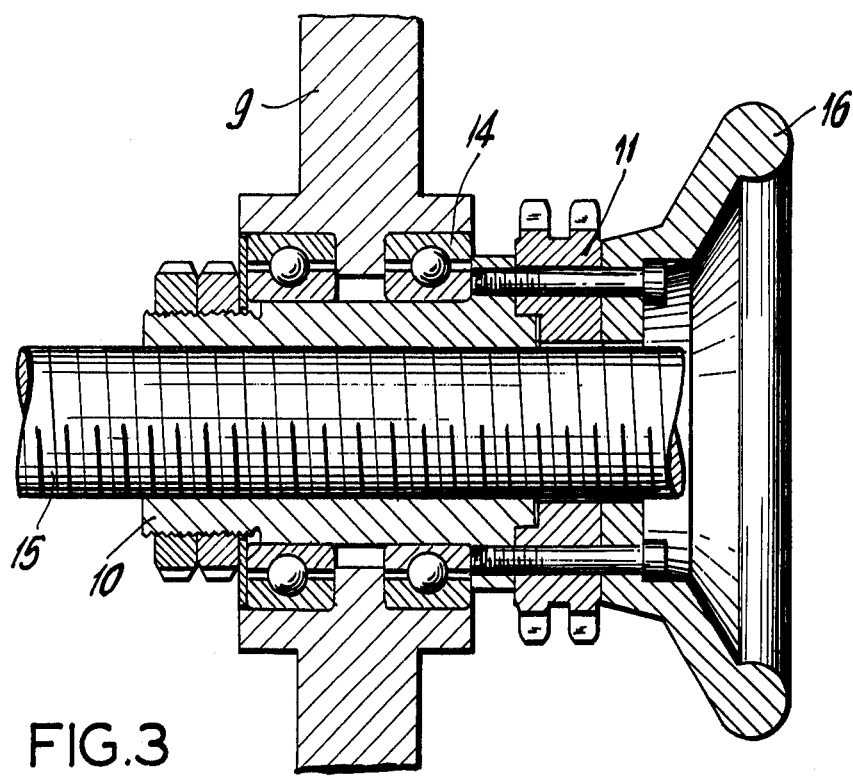
FIG. 3 is an enlarged partial axial sectional view through the screw and nut drive for the movable support.
Figure 4:
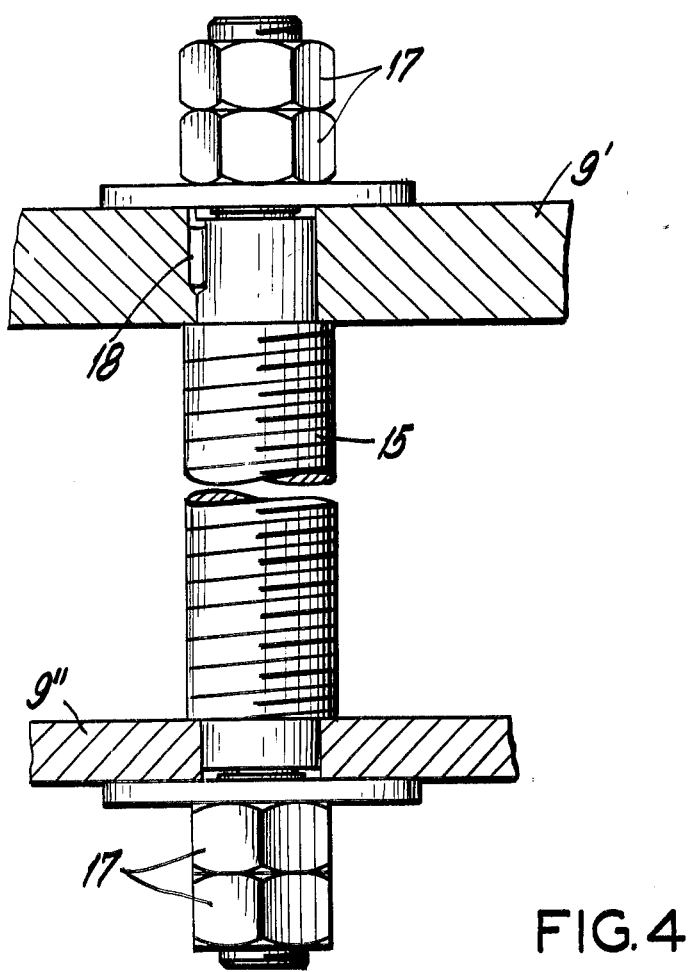
FIG. 4 is a partial horizontal sectional view illustrating the securing of the screws for translation of the movable support.
Figure 5:
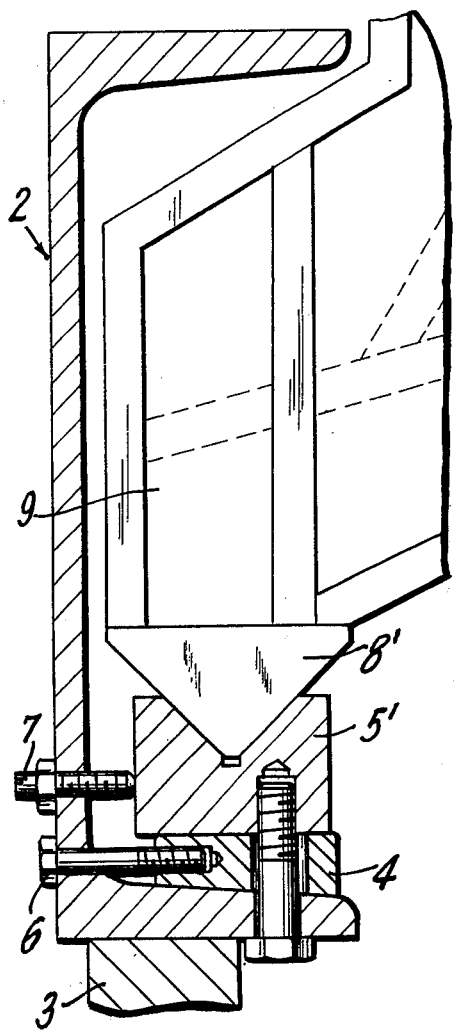
FIG. 5 is a partial vertical transverse sectional view, to a larger scale, illustrating a longitudinal skid arranged inside one channel forming part of the base of the press.

The fixed vertical supports 9' and 9'' serve to support screws 15 which are fixed to the two supports by means of nuts 17, as shown in FIG. 4. Pins or keys 18 prevent any rotation of screws 15. By tightening of the nuts 17, supports 9' and 9'' are fixedly secured to screws 15 thus securing the entire assembly to the base beams 1 and 2 inasmuch as supports 9' and 9'' are, in turn, fixedly secured to beams 1 and 2 at their lower ends.

As best seen in FIGS. 2 and 2a, support 9' is formed with a central aperture 19 for receiving a projection on a half die to be mounted thereon, and around the aperture or hole 19, support 9' is formed with smaller holes 20 for the application of a lubricant injector. In addition, T-shape tracks 21 are provided in supports 9 and 9' for mounting of the dies on the supports. Support 9 is also provided with the central hole 19 and with the lubricant injection openings 20.

Fixed support 9'' is substantially similar to fixed support 9', but does not have the central hole 19 or the tracks 21. Instead, support 9'' is provided with a series of ferrules 22 serving as rabbets of the moveable parts movable the half die anchored on support 9, and also serving for extraction or removal of the half die from the support 9.

By reference to FIG. 2, it will be noted that the three screws 15 are spaced widely apart both horizontally and vertically. One screw 15 is located intermediate the height of support 9' at its lefthand side, as viewed in FIG. 2. The other two screws 15 are mounted, respectively, at the righthand side of support 9', one being located adjacent the extreme upper end of the support and the other being located adjacent the extreme lower end of the support and substantially within channel 1. This latter screw is also shown in FIG. 6.

While a specific embodiment of the invention has been shown and described in detail to illustrate the application of the principles of the invention, it will be understood that the invention may be embodied otherwise without departing from such principles.

What is claimed is:

1. A horizontal die-testing press for adjusting and testing mating die halves for use in die casting, injection molding and the like of metals, metal alloys, and synthetic resin materials, said die-testing press comprising, in combination, an elongated horizontal rigid base; two substantially planar vertical opposed supports mounted on said base for horizontal movement relative to each other; said supports being constructed and arranged for anchoring thereon of respective mating die halves in opposed relation; means operable to move said supports toward and away from each other; guiding means engaged with said supports and maintaining parallelism of said supports during relative horizontal movement thereof; one of said substantially planar vertical supports being fixedly mounted on said base at one end thereof, and the other of said substantially planar vertical supports being mounted on said base for horizontal sliding movement therealong toward and away from said one support; a plurality of nuts rotatably mounted in said movable support; a respective non-rotatable and axially fixed screw threaded through each nut; means operable to rotate said nuts in synchronism with each other to effect horizontal movement of said other movable support toward and away from said one fixed support in parallel orientation thereto; said means for rotating said nuts in synchronism with each other comprising respective sprockets secured to said nuts for rotation therewith, chain means interconnecting all of said sprockets, and means for driving said chain means; said driving means comprising an electric motor; respective hand wheels secured to at least certain of said nuts for manual rotation thereof; and a third substantially planar vertical support fixed to said base at the opposite end thereof; said screws being fixed at their ends to said fixed substantially planar vertical supports, against rotation and against axial displacement; there being three screws located at different levels relative to said base and all located at the maximum distance from the longitudinal axis of said press so as to leave free the central space between the two die half mounting supports to allow an easy mounting and dismounting of the dies both from above the press and from a side thereof, and also to provide easy access for the operator into the press.

2. A horizontal die-testing press, as claimed in claim 1, in which said elongated horizontal rigid base comprises a pair of elongated horizontally oriented rigid channels arranged in facing laterally spaced and parallel relation to each other; respective prismatic cross-section rigid dies extending along and within each channel; and skid means on said other and movable substantially planar vertical support slidably engaging said guides.

3. A horizontal die-testing press, as claimed in claim 2, including adjustable wedge means interposed between each guide and the associated channel and adjustable to effect horizontal alignment of the associated guide.

* * * * *